United States Patent
Koziczynski et al.

(10) Patent No.: US 9,700,304 B2
(45) Date of Patent: Jul. 11, 2017

(54) FILAMENT IMPLANT SYSTEM AND METHOD

(75) Inventors: Pawel W. Koziczynski, Warsaw (PL); Richard L. Grant, Cincinnati, OH (US)

(73) Assignee: Gold Thread LLC, Cincinnati, OH (US)

( * ) Notice: Subject to any disclaimer, the term of this patent is extended or adjusted under 35 U.S.C. 154(b) by 0 days.

(21) Appl. No.: 12/762,543

(22) Filed: Apr. 19, 2010

(65) Prior Publication Data
US 2011/0257581 A1    Oct. 20, 2011

(51) Int. Cl.
| | | |
|---|---|---|
| *A61M 5/32* | (2006.01) | |
| *A61F 13/20* | (2006.01) | |
| *A61B 17/06* | (2006.01) | |
| A61B 17/00 | (2006.01) | |
| A61F 2/00 | (2006.01) | |
| A61B 90/00 | (2016.01) | |

(52) U.S. Cl.
CPC ........ *A61B 17/06* (2013.01); *A61B 17/06109* (2013.01); *A61B 2017/00429* (2013.01); *A61B 2017/00455* (2013.01); *A61B 2017/00792* (2013.01); *A61B 2017/06009* (2013.01); *A61B 2017/06042* (2013.01); *A61B 2017/06047* (2013.01); *A61B 2017/06052* (2013.01); *A61B 2090/062* (2016.02); *A61F 2/0059* (2013.01)

(58) Field of Classification Search
CPC .............. A61B 17/06; A61B 17/06109; A61B 2017/00429; A61B 2017/00455; A61B 2017/00792; A61B 2017/06009; A61B 2017/06042; A61B 2017/06047; A61B 2017/06052; A61B 2090/062; A61F 2/0059

USPC .......................................................... 604/272
See application file for complete search history.

(56) References Cited

U.S. PATENT DOCUMENTS

| | | | |
|---|---|---|---|
| 2,711,733 A | 6/1955 | Jacoby | |
| 3,921,632 A | 11/1975 | Bardani | |
| 4,490,139 A | 12/1984 | Huizenga | |
| 5,342,376 A | 8/1994 | Ruff | |
| 5,971,993 A | 10/1999 | Hussein et al. | |
| (Continued) | | | |

FOREIGN PATENT DOCUMENTS

| | | |
|---|---|---|
| WO | WO 98/30274 | 7/1998 |
| WO | WO 2005/117722 | 12/2005 |

OTHER PUBLICATIONS

Adamyan, A.A. et al., "Clinical Aspects of Facial Skin Reinforcement with Special (Gold) Surgical Filaments," Ann Plast Reconstr Aesthetic Surg 3 (1998).

(Continued)

*Primary Examiner* — Jason Flick
(74) *Attorney, Agent, or Firm* — Walters & Wasylyna LLC

(57) ABSTRACT

A filament implant system including an insertion needle including an elongated body defining a longitudinal axis and having a distal end and a proximal end, the distal end of the elongated body including a penetrating tip, and a filament releasably connected to the insertion needle such that the filament is engaged with the insertion needle when the insertion needle is advanced into tissue distally along the longitudinal axis and the filament is disengaged from the insertion needle when the insertion needle is withdrawn from the tissue proximally along the longitudinal axis.

9 Claims, 15 Drawing Sheets

(56) References Cited

U.S. PATENT DOCUMENTS

| | | | |
|---|---|---|---|
| 6,086,578 A | 7/2000 | Adamyan et al. | |
| 6,238,415 B1 | 5/2001 | Sepetka et al. | |
| 6,258,119 B1 * | 7/2001 | Hussein | A61F 2/06 606/108 |
| 6,361,547 B1 | 3/2002 | Hieshima | |
| 6,599,310 B2 | 7/2003 | Leung et al. | |
| 6,620,152 B2 | 9/2003 | Guglielmi | |
| 6,620,170 B1 | 9/2003 | Ahern | |
| 6,719,805 B1 | 4/2004 | Ahern | |
| 6,848,152 B2 | 2/2005 | Genova et al. | |
| 6,855,160 B1 | 2/2005 | Gambale et al. | |
| 6,986,784 B1 * | 1/2006 | Weiser et al. | 623/1.1 |
| 7,204,847 B1 | 4/2007 | Gambale | |
| 7,225,512 B2 | 6/2007 | Genova et al. | |
| 7,226,468 B2 | 6/2007 | Ruff | |
| 7,513,904 B2 * | 4/2009 | Sulamanidze et al. | 606/224 |
| 7,559,952 B2 | 7/2009 | Pinchuk | |
| 7,601,164 B2 | 10/2009 | Wu | |
| 7,613,523 B2 | 11/2009 | Eggers et al. | |
| 7,624,487 B2 | 12/2009 | Trull et al. | |
| 2003/0229321 A1 * | 12/2003 | Simon | A61B 17/3417 604/272 |
| 2004/0267315 A1 | 12/2004 | Wolf et al. | |
| 2005/0203576 A1 | 9/2005 | Sulamanidze et al. | |
| 2007/0023974 A1 | 2/2007 | Wu | |
| 2009/0210003 A1 | 8/2009 | Sulamanidze et al. | |
| 2010/0331612 A1 | 12/2010 | Lashinski et al. | |
| 2011/0046632 A1 * | 2/2011 | Quevedo | A61B 17/3472 606/102 |

OTHER PUBLICATIONS

Haddad, Guy et al., Excerpts from "Jeunesse Pour Tous" (1993).
International search report and written opinion issued in PCT/US2011/032243 (Jun. 30, 2011).

* cited by examiner

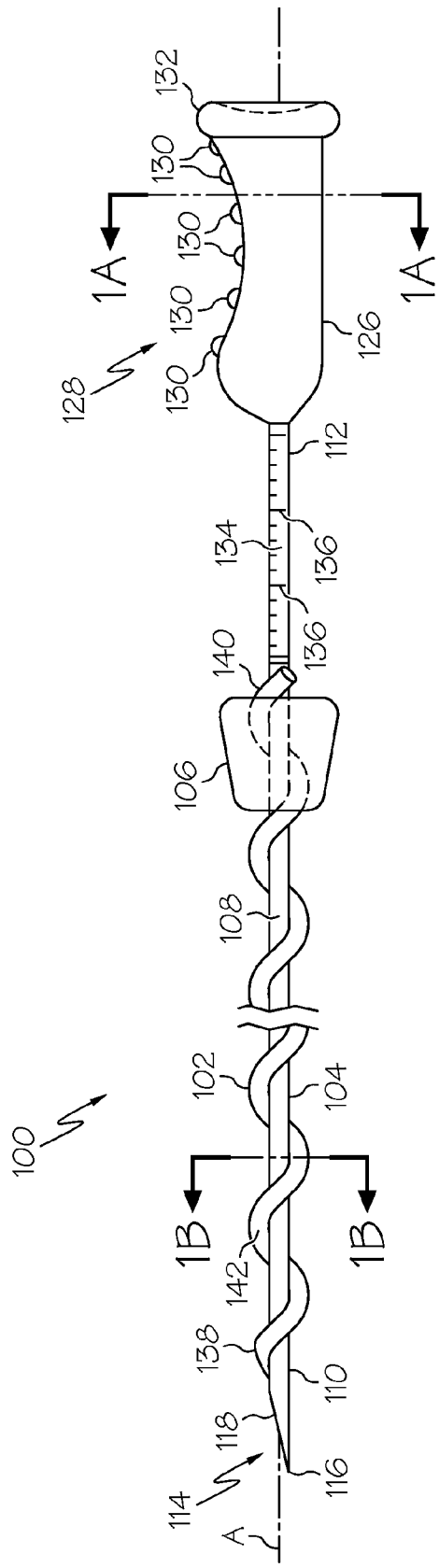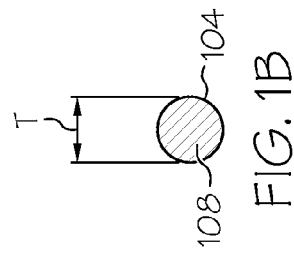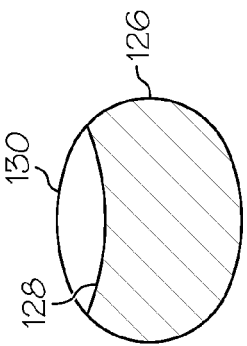

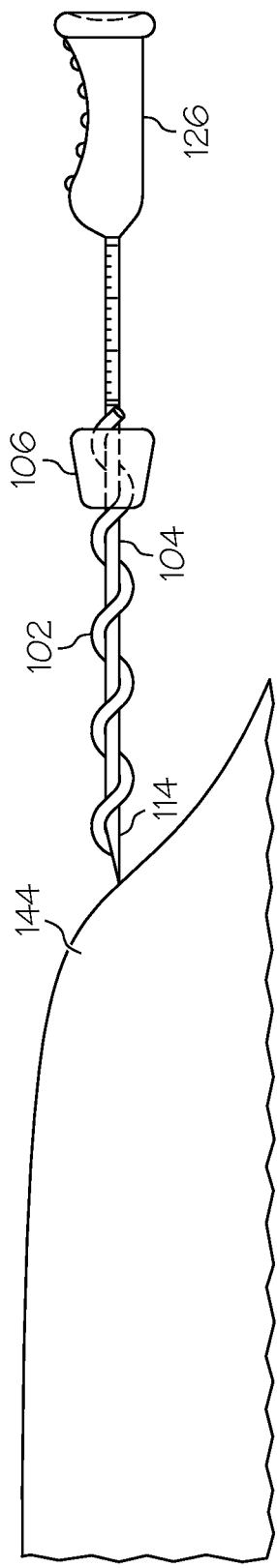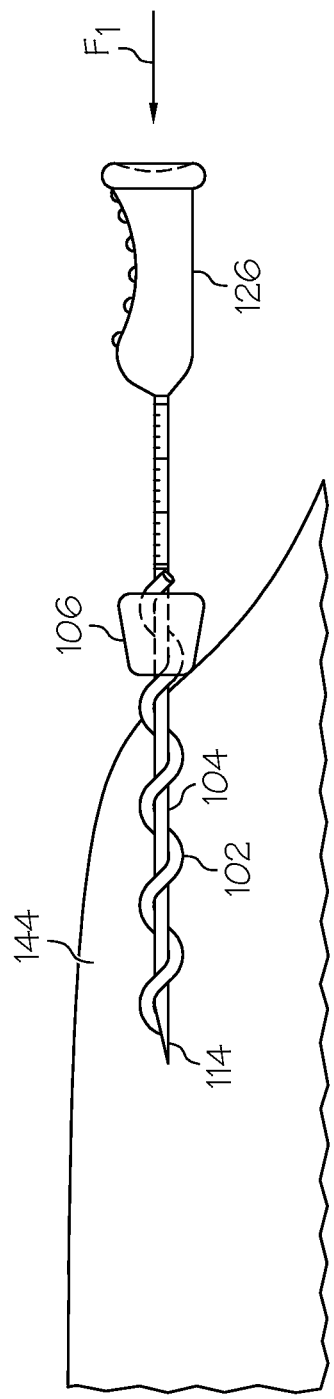
FIG. 4A
FIG. 4B

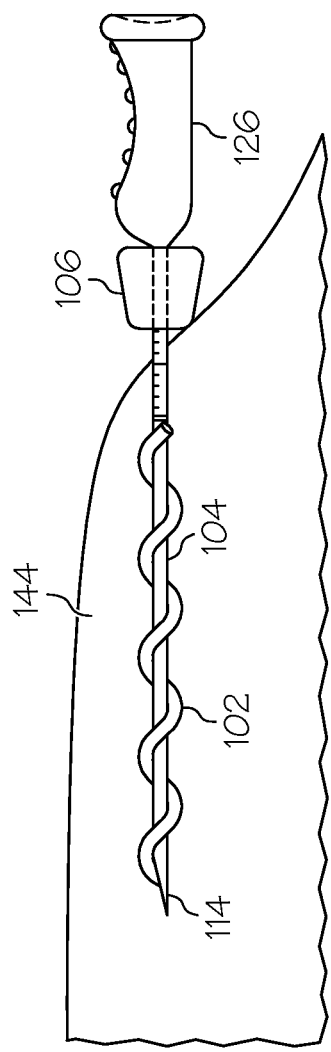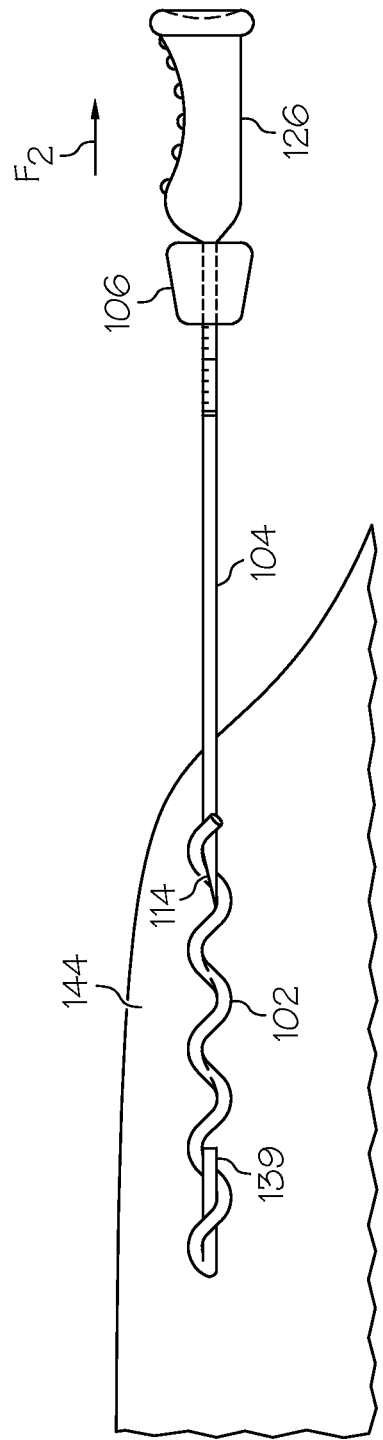
FIG. 4C
FIG. 4D

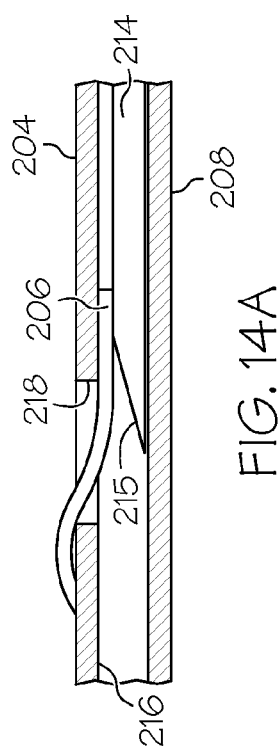
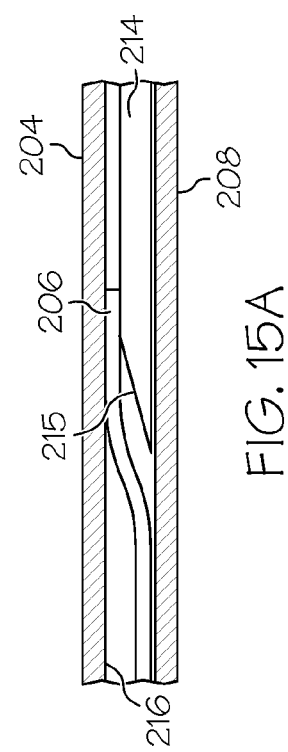
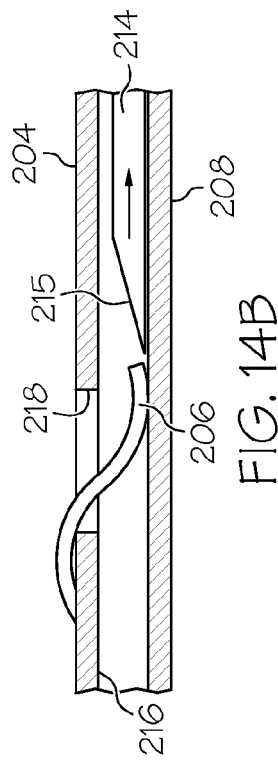
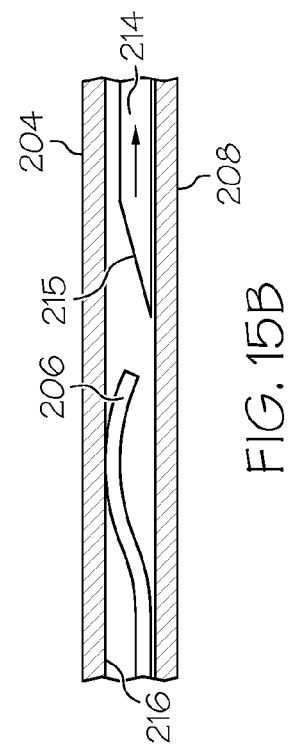
FIG. 14A
FIG. 14B
FIG. 15A
FIG. 15B

FILAMENT IMPLANT SYSTEM AND METHOD

FIELD

This application relates to the implantation of filaments and, more particularly, to systems and methods for intradermally implanting filaments into body tissue, such as mammalian skin.

BACKGROUND

In cosmetic and plastic surgery, filaments, such as gold filaments, are intradermally implanted into the skin, typically in the vicinity of the face, neck, arms and legs, to rejuvenate the skin. Specifically, the implantation of filaments into the skin has been shown to improve circulation, advantageously induce collagen formation and advantageously lift the skin and underlying soft tissue, thereby potentially reducing or eliminating visible signs of aging, such as wrinkles and ptosis.

The conventional technique for implanting a filament into the skin involves the use of a needle having a filament connected thereto, either fixedly or by threading the filament through an eyehole in the needle. With the filament attached to the needle, the needle may be advanced through the skin with the filament trailing behind in a manner similar to needle-and-tread sewing. Once the needle has pulled the filament a sufficient distance into the skin, and the filament is positioned at the desired location in the skin, the filament may be detached from the needle (e.g., by cutting the filament) and the needle may be further advanced and withdrawn from the skin, leaving the filament behind.

Thus, the conventional filament implantation technique requires the formation of at least two incisions per filament implanted: a first incision where the needle enters the skin and a second incision where the needle exits the skin. Each incision creates trauma and presents the risk of infection.

Accordingly, those skilled in the art continue to explore new techniques for implanting filaments into body tissue.

SUMMARY

In one aspect, the disclosed filament implant system may include an insertion needle including an elongated body defining a longitudinal axis and having a distal end and a proximal end, the distal end of the elongated body including a penetrating tip, and a filament releasably connected to the insertion needle such that the filament is engaged with the insertion needle when the insertion needle is advanced into tissue distally along the longitudinal axis and the filament is disengaged from the insertion needle when the insertion needle is withdrawn from the tissue proximally along the longitudinal axis.

In another aspect, the disclosed filament implant system may include an insertion needle including an elongated body defining a longitudinal axis and having a distal end and a proximal end, the distal end of the elongated body including a penetrating tip having a recess formed therein, and a filament wrapped around the elongated body and including a distal end and a proximal end, wherein the distal end of the filament is received in the recess.

In another aspect, disclosed is a method for implanting a filament in body tissue, wherein the method includes the steps of (1) providing a filament implant system that includes an insertion needle and a filament releasably engaged with the insertion needle, the insertion needle including an elongated body having a distal end and a proximal end, the distal end of the elongated body including a penetrating tip, (2) advancing the insertion needle into the body tissue, wherein the filament travels with the insertion needle during the advancing step, and (3) withdrawing the insertion needle from the body tissue, wherein the filament is disengaged from the insertion needle during the withdrawing step such that the filament remains in the body tissue.

Other aspects, implementations and expressions of the disclosed filament implant system and method will become apparent from the following description, the accompanying drawings and the appended claims.

BRIEF DESCRIPTION OF THE DRAWINGS

FIG. 1 is a side elevational view of a filament implant system in accordance with a first aspect of the disclosure;

FIG. 1a is a cross-sectional view of the handle of the insertion needle of the filament implant system of FIG. 1;

FIG. 1b is a cross-sectional view of the elongated body of the insertion needle of the filament implant system of FIG. 1;

FIGS. 4a-d are side elevational views of a filament being implanted into body tissue using the filament implant system of FIG. 1;

FIG. 7b is a cross-sectional view of the distal end of the filament implant system of FIG. 7a;

FIG. 8b is a cross-sectional view of the distal end of the filament implant system of FIG. 8a;

FIG. 11 is a cross-sectional view of a portion of the distal end of the filament implant system shown in FIG. 10a;

FIG. 14a is a cross-sectional view of a portion of the filament implant system of FIG. 13a;

FIG. 14b is a cross-sectional view of the portion of the filament implant system of FIG. 13b, wherein the filament in a disengaged from the insertion needle;

FIG. 15a is a cross-sectional view of an alternative implementation of the portion shown in FIG. 14a;

FIG. 15b is a cross-sectional view of the portion of the filament implant system of FIG. 15a, wherein the filament in a disengaged from the insertion needle;

FIG. 16b is a cross-sectional view of the portion of the filament implant system of FIG. 16a;

FIG. 17b is a cross-sectional view of the portion of the filament implant system of FIG. 17a.

DETAILED DESCRIPTION

Figure 2:
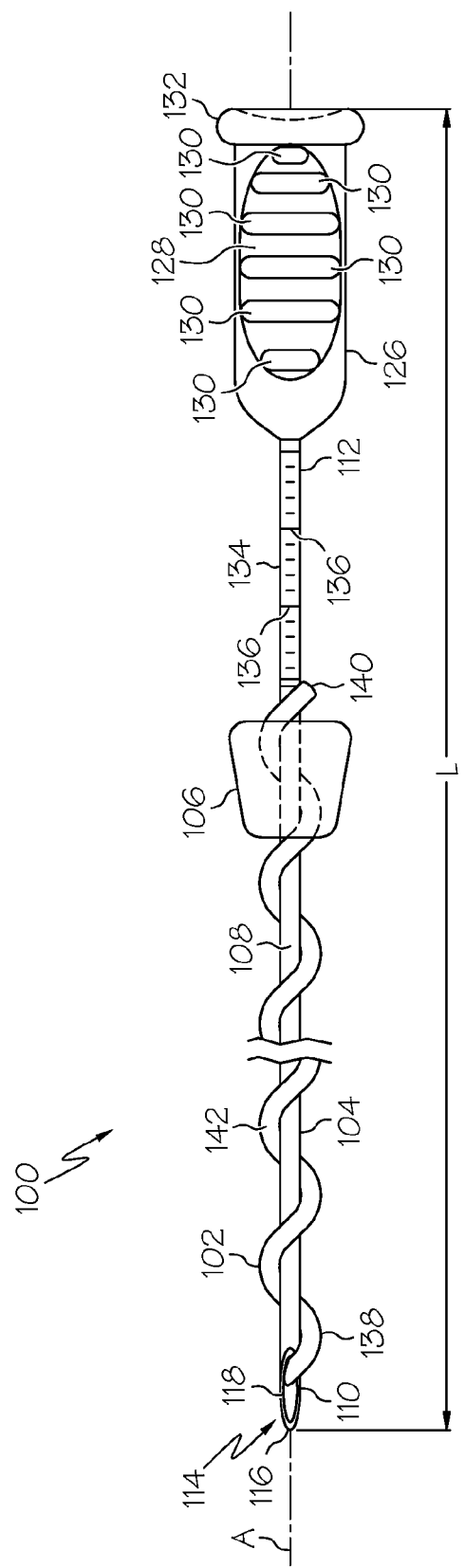
FIG. 2 is a top plan view of the filament implant system of FIG. 1.

As shown in FIGS. 1 and 2, one aspect of the disclosed filament implant system, generally designated 100, may include a filament 102 and an insertion needle 104. Optionally, the filament implant system 100 may additionally include a fastener 106 for securing the filament 102 relative to the insertion needle 104.

The insertion needle 104 may include an elongated body 108 having distal end 110 and a proximal end 112, and may define a longitudinal axis A. The elongated body 108 of the insertion needle 104 may have a length L (FIG. 2) of, for example, about 5 centimeters to about 13 centimeters and a cross-sectional thickness T (FIG. 1b) of, for example, about 0.2 millimeters to about 0.7 millimeters. As a specific example, the elongated body 108 of the insertion needle 104 may be 25 gauge, 27 gauge, 29 gauge or smaller to minimize trauma during insertion. The elongated body 108 of the insertion needle 104 may be formed from a generally solid yet flexible, biocompatible material, such a surgical-grade stainless steel, nickel-titanium alloy or the like.

As shown in FIG. 1b, the elongated body 108 of the insertion needle 104 may have a generally solid core, thereby providing additional stiffness to the insertion needle 104. However, those skilled in the art will appreciate that the elongated body 108 may be formed as a hollow cannula or needle (e.g., a hypodermic needle) without departing from the scope of the present disclosure. Aspects and implementations of the disclosure that employ hollow, tubular elongated bodies are described in greater detail below.

Figure 5:
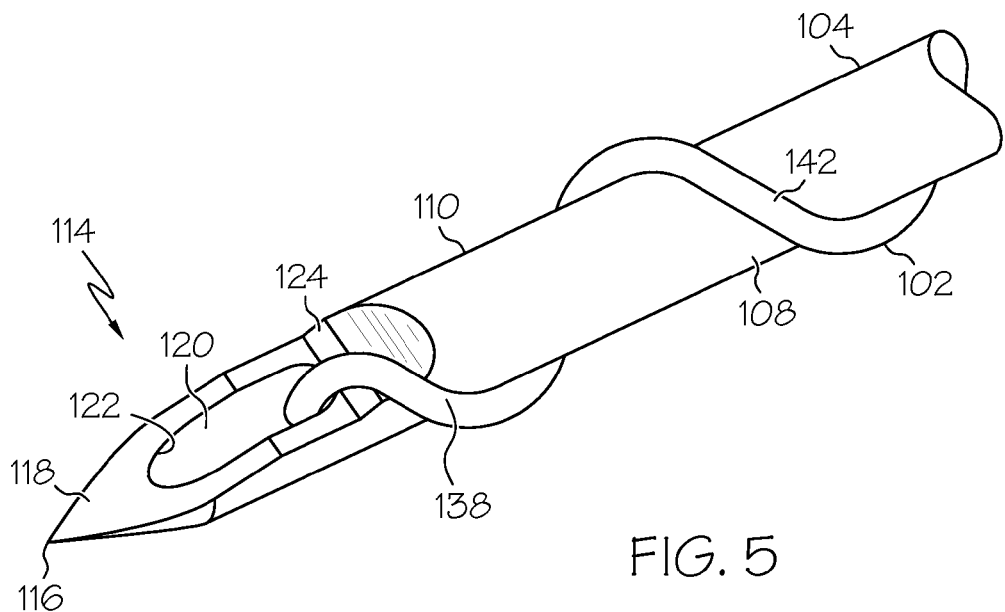
FIG. 5 is an isometric view of the distal end of the filament implant system of FIG. 1 in accordance with a first implementation of the disclosure.
Figure 6:
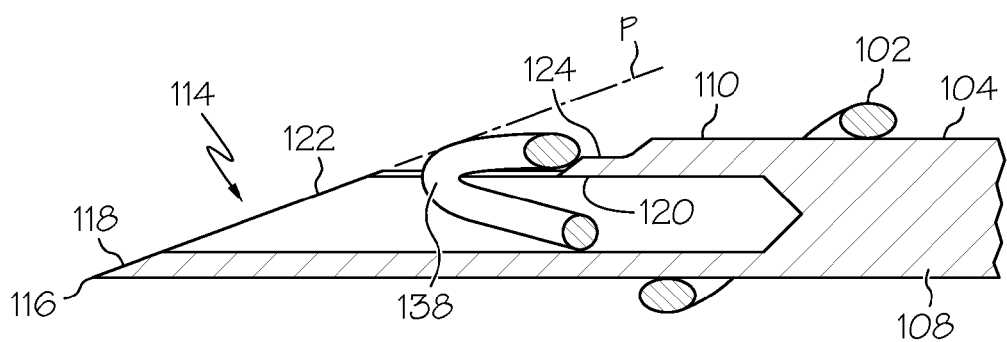
FIG. 6 is a cross-sectional view of the distal end of the filament implant system of FIG. 5.

Referring to FIGS. 5 and 6, the distal end 110 of the elongated body 108 of the insertion needle 102 may include a penetrating tip 114. The penetrating tip 114 may be integral with the elongated body 108 or may be pre-formed and connected to the elongated body 108. The penetrating tip 114 may include a distal-most point 116, a beveled face 118 and a recess 120. The recess 120 may include an opening 122 in the beveled face 118 and may extend proximally into the elongated body 108 from the beveled face 118. In one particular expression, as shown in FIGS. 5 and 6, the recess 120 may be a bore (e.g., a relatively short, cylindrical bore) that extends proximally through the distal end 110 of the elongated body 108 along the longitudinal axis A of the body 108. In another particular expression, the recess 120 may be a lumen (described in greater detail below) that extends through the elongated body 108 from the distal end 110 of the elongated body 108 to (or proximate) the proximal end 112 of the elongated body 108.

Optionally, the penetrating tip 114 may additionally include a relief 124 where the external surface of the body 108 is displaced radially inward from the plane P (FIG. 6) defined by the beveled face 118. The opening 122 of the recess 120 may extend longitudinally through all or a portion of the relief 124.

While the penetrating tip 114 is shown and described as having a beveled face 118, those skilled in the art will appreciate that various penetrating tips are known in the art and can be modified to include a recess 120 and, optionally, a relief 124, without departing from the scope of the present disclosure. For example, alternative expressions of the penetrating tip 114 may include a lancet tip, cutting tip, a Huber point or a pencil point.

Referring back to FIGS. 1 and 2, the proximal end 112 of the elongated body 108 of the insertion needle 104 may include a handle 126 connected thereto. The handle 126 may be any structure that facilitates gripping the insertion needle 104. For example, the handle 126 may be a body (e.g., a generally cylindrical body) having a greater cross-sectional thickness than the elongated body 108. Furthermore, the handle 126 may be formed as a separate piece that has been fixedly connected to the elongated body 108 or, alternatively, may be integrally formed with the elongated body 108.

In one optional expression, as shown in FIGS. 1, 1a and 2, the handle 126 may include an alignment feature 128 that may be circumferentially oriented relative to the penetrating tip 114, thereby facilitating tactile orientation of the penetrating tip 114. For example, the alignment feature 128 may be a recessed portion in the handle 126. The alignment feature 128 may also include a series of ribs 130 to aid in gripping.

In another optional expression, the handle 126 may include a cupped proximal end 132. Advantageously, the cupped proximal end 132 of the handle 126 may facilitate applying a distal, longitudinal force to the insertion needle 104 to push the insertion needle 104 into tissue (e.g., mammalian skin), as shown in FIGS. 4a and 4b. Additionally, the cupped proximal end 132 of the handle 126 may aid in gripping the insertion needle 104, particularly when withdrawing the insertion needle 104 from tissue, as shown in FIG. 4d.

The elongated body 108 of the insertion needle 104 may further include a depth scale 134. The depth scale 134 may be disposed at or adjacent to the proximal end 112 of the elongated body 108, and may be disposed distal to the handle 126. The depth scale 134 may be provided with indicia 136, such as circumferential lines, indicative of the distance from the penetrating tip 114. Therefore, the depth scale 134 may be used to determine the distance the insertion needle 104 has been inserted into tissue, as shown in FIG. 4c.

The filament 102 may be any elongated filament, fiber, thread, suture, wire, cable, tube or the like, and may include a distal end 138 and a proximal end 140. The filament 102 may have various lengths and cross-sectional thicknesses, which may be selected by the user based on the procedure being performed, the target tissue being treated, the type of filament being used, among other factors that will be appreciated by those skilled in the art. For example, the filament 102 may have a length of about 5 centimeters to about 30 centimeters. The cross-sectional thickness of the filament 102 may be less (e.g., 70 percent or less, 50 percent or less, 30 percent or less, or even 10 percent or less) than the cross-sectional thickness T (FIG. 1b) of the elongated body 108. For example, the cross-sectional thickness of the filament 102 may be about 0.03 millimeters to about 0.3 millimeters.

In a first expression, the filament 102 may be formed from or may include a metal, such as gold (e.g., 24 karat gold), stainless steel, titanium, titanium alloy (e.g., nickel-titanium alloy) and/or platinum. In a second expression, the filament 102 may be formed from or may include a synthetic polymer, such as polypropylene, polyethylene, nylon and/or polyester. In a third expression, the filament 102 may be formed from or may include a natural material, such as animal tissue, gut, cotton and/or silk. In a fourth expression, the filament 102 may be formed from or may include a bioabsorbable material, such as polymers and copolymers of glycolic acid, lactic acid and/or caprolactone.

The filament 102 may be a monofilament or a multifilament, such as a braded filament or a twisted filament, and may have various cross-sectional profiles, such as round, square or flat. The selection of the composition and the structure of the filament 102 is within the grasp of those skilled in the art.

Optionally, the filament 102 may be configured as a drug delivery device. Specifically, a drug, a biologic or other therapeutic agent may be incorporated into the filament 102 for delivery to a patient in need thereof upon implantation of the filament 102 into tissue. For example, a drug delivering filament 102 may be formed by encapsulating a gel or liquid in a hollow bead or hollow filament.

The filament 102 may be releasably engaged with the insertion needle 104 such that the filament 102 travels with the insertion needle 104 while the insertion needle 104 is being distally advanced into body tissue, as shown in FIGS. 4a-4c. Then, the filament 102 may be disengaged from the insertion needle 104 when the insertion needle 104 is withdrawn from the tissue, as shown in FIG. 4d.

Referring to FIGS. 5 and 6, in one particular implementation, the filament 102 may be releasably engaged with the insertion needle 104 by inserting the distal end 138 of the filament 102 into the recess 120 in the penetrating tip 114 of the insertion needle 104. As such, the filament 102 may included a hooked portion 139 (FIG. 4d) that hooks onto the distal end 110 of the insertion needle 104. As shown in FIG. 6, the relief 124 may have a sufficient depth such that the filament 102 remains below the plane P defined by the beveled surface 118 of the penetrating tip 114, thereby minimizing drag caused by the filament 102 during insertion into tissue.

Referring back to FIGS. 1 and 2, with the distal end 138 of the filament 102 received in the recess 120 in the penetrating tip 114, the trailing portion 142 of the filament 102 (i.e., the portion of the filament 102 proximal to the distal end 138) may be external of the insertion needle 104. In one expression, the trailing portion 142 of the filament 102 may extend proximally generally parallel with the elongated body 108 of the insertion needle 104, and the proximal end 140 of the filament 102 may be secured to the insertion needle 104 by the fastener 106. In another expression, as shown in FIGS. 1 and 2, the trailing portion 142 of the filament 102 may be wrapped (e.g., as a spiral or helical coil) around the elongated body 108 of the insertion needle 104. Those skilled in the art will appreciate that forming the filament 102 into a spiral or coil shape may allow for use of a filament 102 having a longer length and may expose a greater surface area of the filament 102 to the body tissue, thereby advantageously assisting in the formation of collagen and improving the lifting effect.

The fastener 106 may be any device capable of holding the filament 102 relative to the insertion needle 104. For example, the fastener 106 may be a circumferential band, ring (e.g., a rubber O-ring) or block of resilient material (e.g., silicone or elastomer) received over the elongated body 108 of the insertion needle 104 to secure the proximal end 140 of the filament 102 to the body 108 during shipping, handling and insertion in the tissue. The fastener 106 may also be a clamp-type device. Of course, multiple fasteners 106 may be used to secure the filament 102 to the insertion needle 104 at multiple points along the elongated body 108. As shown in FIG. 4c, the fastener 106 may be withdrawn in the proximal direction to release the proximal end 140 of the filament 102 from the insertion needle 104, while also functioning as a tissue stop.

As shown in FIGS. 4a-4d, the filament implant system 100 may be used to implant a filament 102 into body tissue 144. Referring to FIG. 4a, the filament implant system 100 may be aligned with the target tissue 144. As shown in FIG. 4b, a force (arrow $F_1$) may be applied to the handle 126 of the insertion needle 104 to urge the penetrating tip 114 of the insertion needle 104 into the tissue 144. Since the filament 102 is releasably engaged with the insertion needle 104, the filament 102 travels with the insertion needle during insertion. The position of the fastener 106 may prevent distal insertion beyond a pre-determined point. As shown in FIG. 4c, with the fastener 106 proximally withdrawn from the filament 102, the insertion needle 104 may be further advanced into the tissue 144. Finally, once the filament 102 is at the desired location in the tissue 144, the insertion needle 104 may be withdrawn by applying an opposite force (arrow $F_2$) to the handle 126. When the withdrawing force (arrow $F_2$) is applied, the force of the tissue 144 closing on the filament implant system 100 engages the filament 102 such that the filament 102 is held in place while the insertion needle 104 is withdrawn relative to the filament 102 and the tissue 144.

Figure 3:
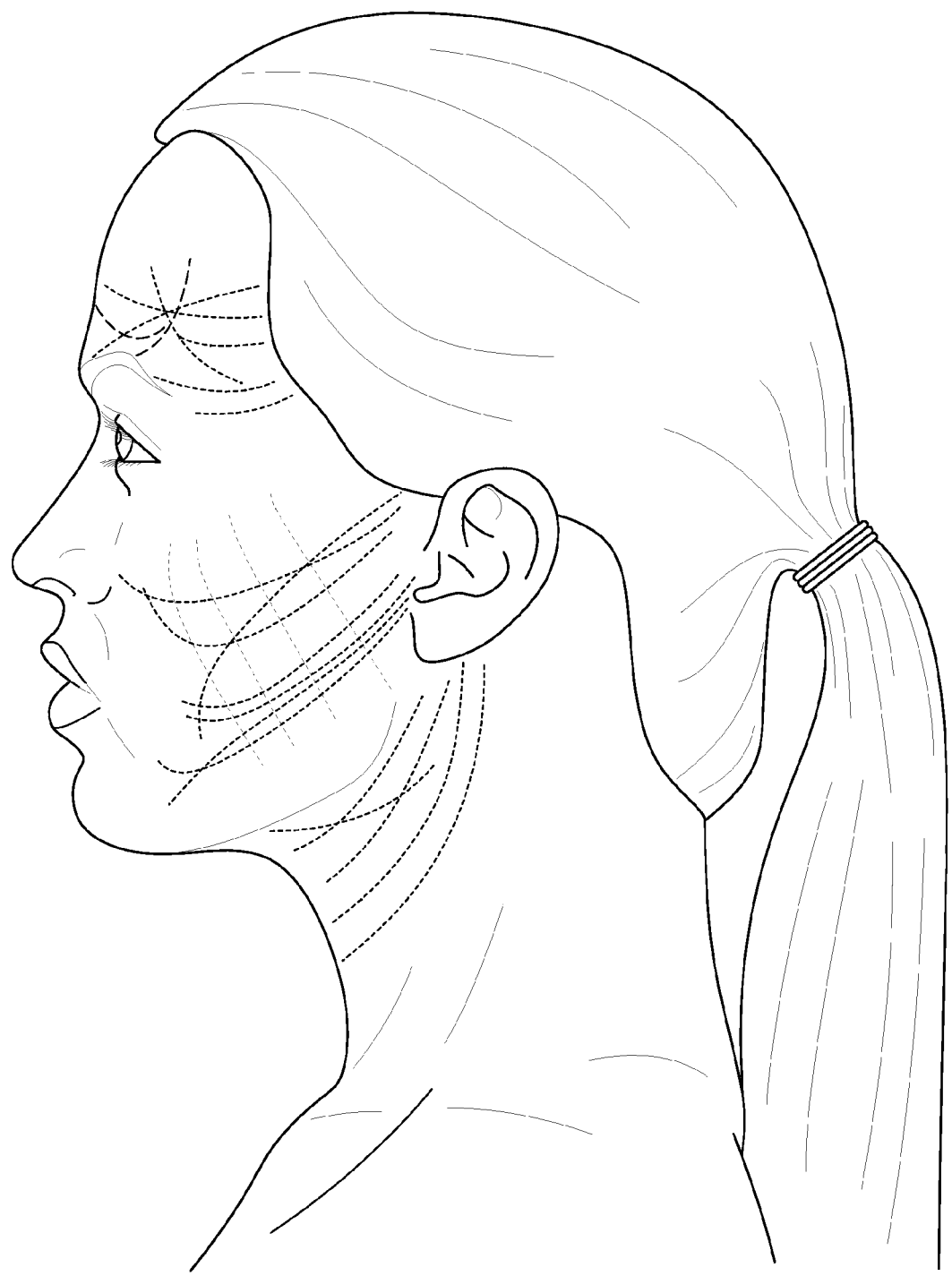
FIG. 3 is a side view of a human face including filaments that have been implanted with the filament implant system of FIG. 1.

Accordingly, as shown in FIG. 3, multiple filaments 102 (shown as broken lines in FIG. 3) may be implanted in patient tissue, such as intradermally into the skin, to rejuvenate the tissue. Optionally, multiple filaments 102 may be implanted using a single entry point without ever creating an exit wound.

Figure 7A:
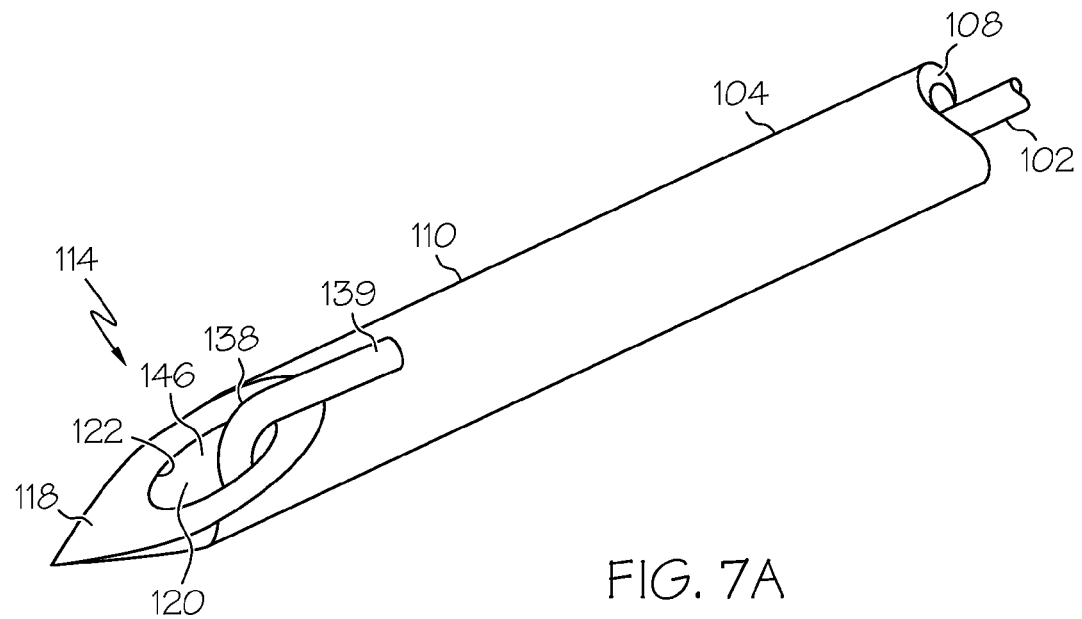
FIG. 7a is an isometric view of a distal end of a filament implant system in accordance with a first alternative implementation of the disclosure.
Figure 7B:
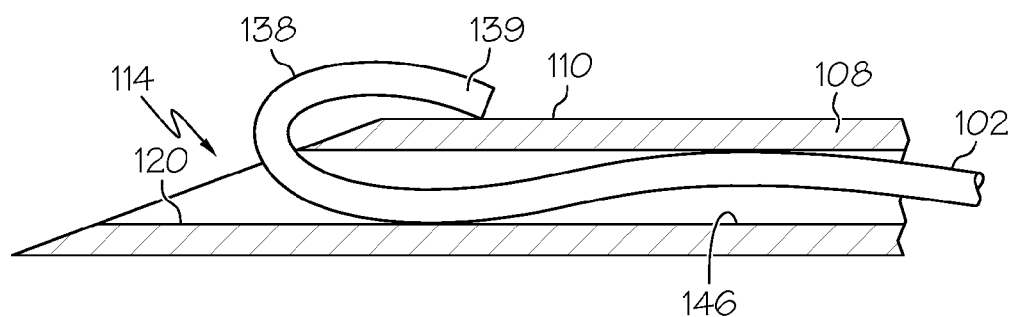

Referring to FIGS. 7a and 7b, in a first alternative implementation, the recess 120 in the distal end 110 of the elongated body 108 of the insertion needle 104 may extend longitudinally as a lumen 146 through the elongated body 108. The opening 122 in the penetrating tip may serve as an opening to the lumen 146. The filament 102 may extend through the lumen 146 such that the distal end 138 of the filament 102 exits the opening 122 and is hooked (by way of hooked portion 139) onto the distal end 138 of the insertion needle 104, thereby releasably engaging the filament 102 with the insertion needle 104.

Thus, during insertion, engagement between the filament 102 and the insertion needle 104 is maintained by pressure from the tissue (not shown) during insertion into body tissue. Then, when the insertion needle 104 is retracted, the distal end 138 of the filament 102 may catch the surrounding tissue and may pull the filament 102 out of the lumen 146 of the insertion needle 104, thereby releasing the filament 102 from the insertion needle 104 such that the filament may remain in the tissue at the desired location.

Figure 8A:
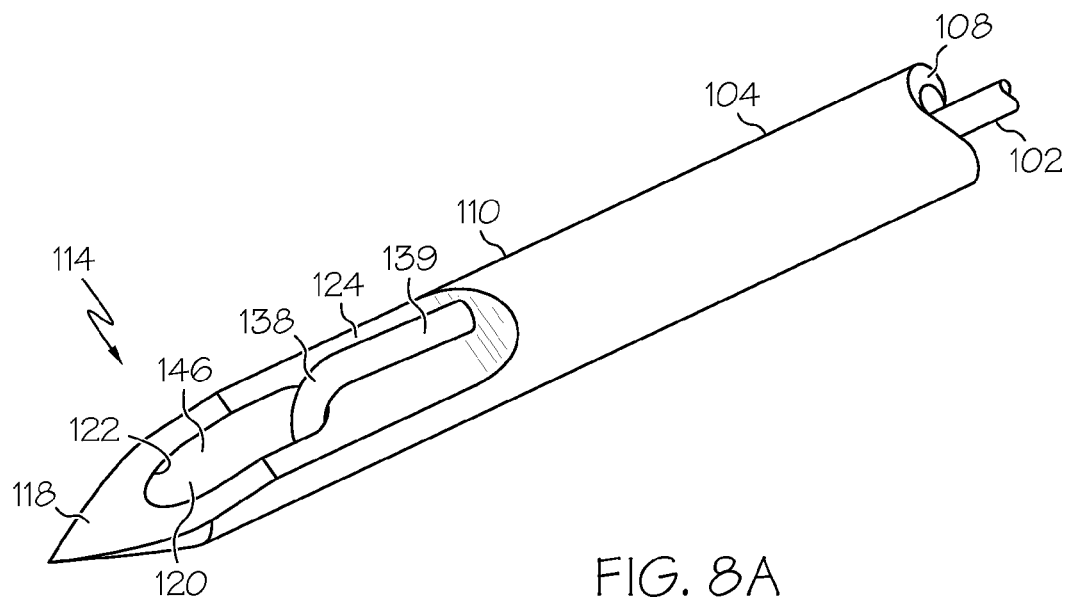
FIG. 8a is an isometric view of a distal end of a filament implant system in accordance with a second alternative implementation of the disclosure.
Figure 8B:
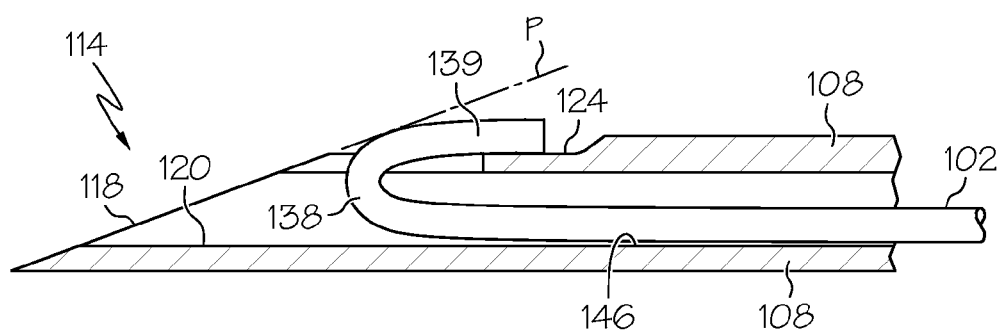

Referring to FIGS. 8a and 8b, in a second alternative implementation, the filament 102 may extend through the lumen 146 in the insertion needle 104 in a manner similar to the implementation shown in FIGS. 7a and 7b. However, in the implementation of FIGS. 8a and 8b, the penetrating tip 114 of the insertion needle 104 may additionally include a relief 124 such that the hooked portion 139 of the distal end 138 of the filament 102 is positioned below the plane P defined by the beveled surface 118 of the penetrating tip 114, thereby minimizing drag caused by the filament 102 during insertion into tissue.

Figure 9A:
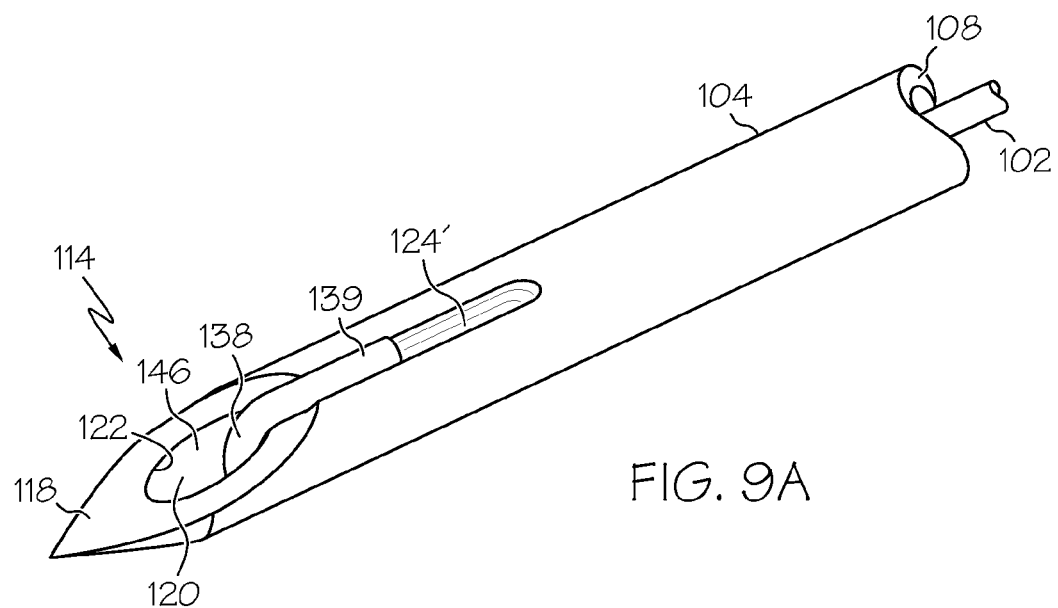
FIG. 9a is an isometric view of a distal end of a filament implant system in accordance with a third alternative implementation of the disclosure.
Figure 9B:
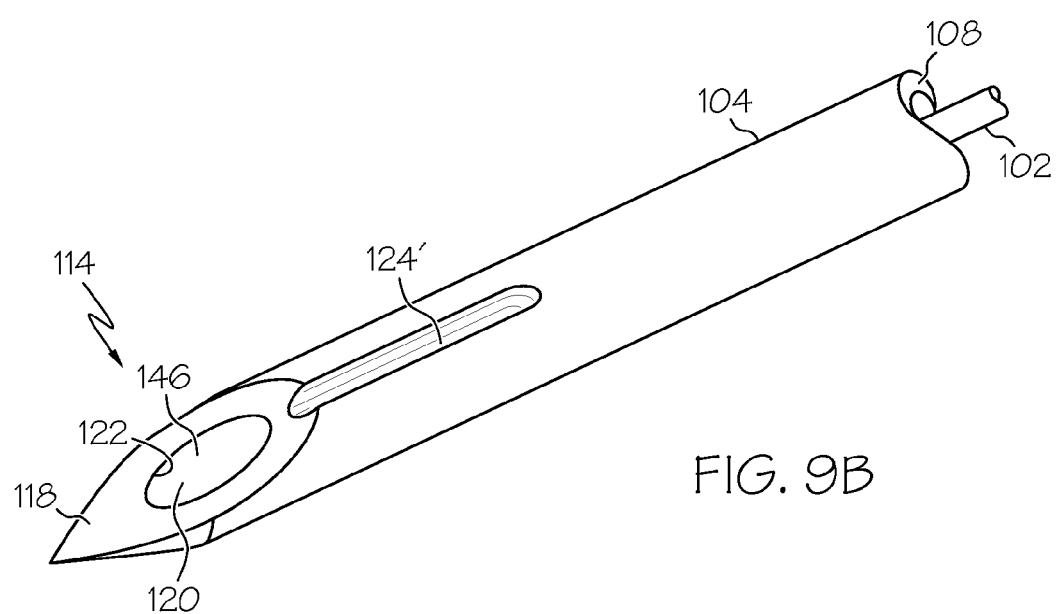
FIG. 9b is an isometric view of the distal end of the filament implant system of FIG. 9a, shown with the filament removed.

Referring to FIGS. 9a and 9b, in a third alternative implementation, the filament 102 may extend through the lumen 146 in the insertion needle 104 in a manner similar to the implementation shown in FIGS. 8a and 8b. However, in the implementation of FIGS. 9a and 9b, the relief 124' may be sized and shaped to closely receive the hooked portion 139 of the distal end 138 of the filament 102.

Figure 10A:
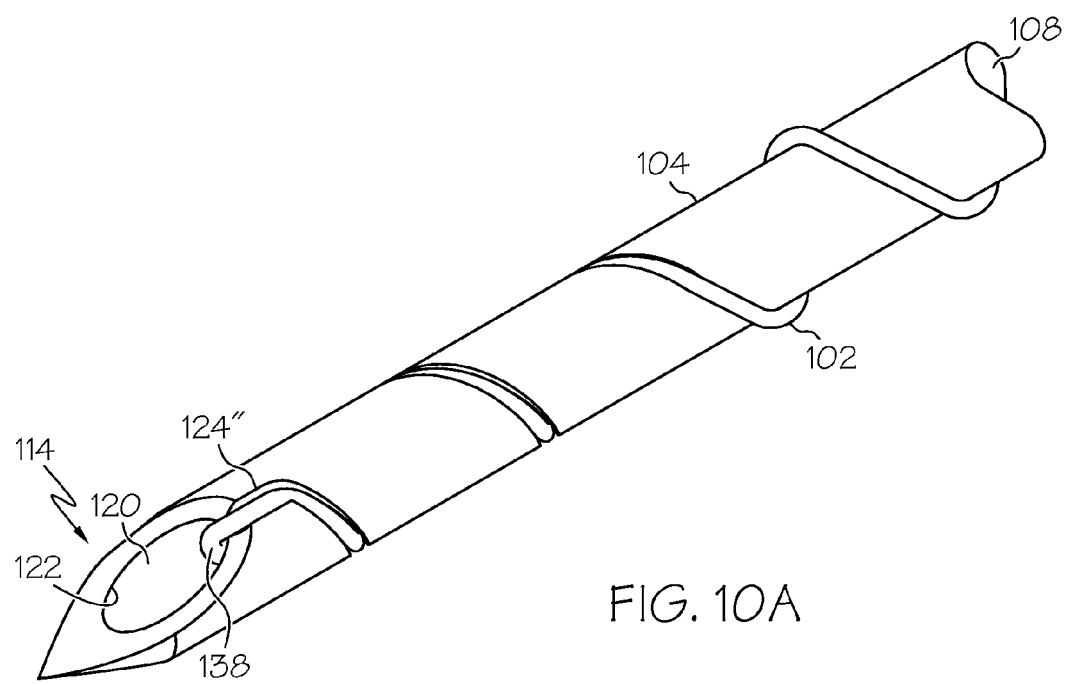
FIG. 10a is an isometric view of a distal end of a filament implant system in accordance with a fourth alternative implementation of the disclosure.
Figure 10B:
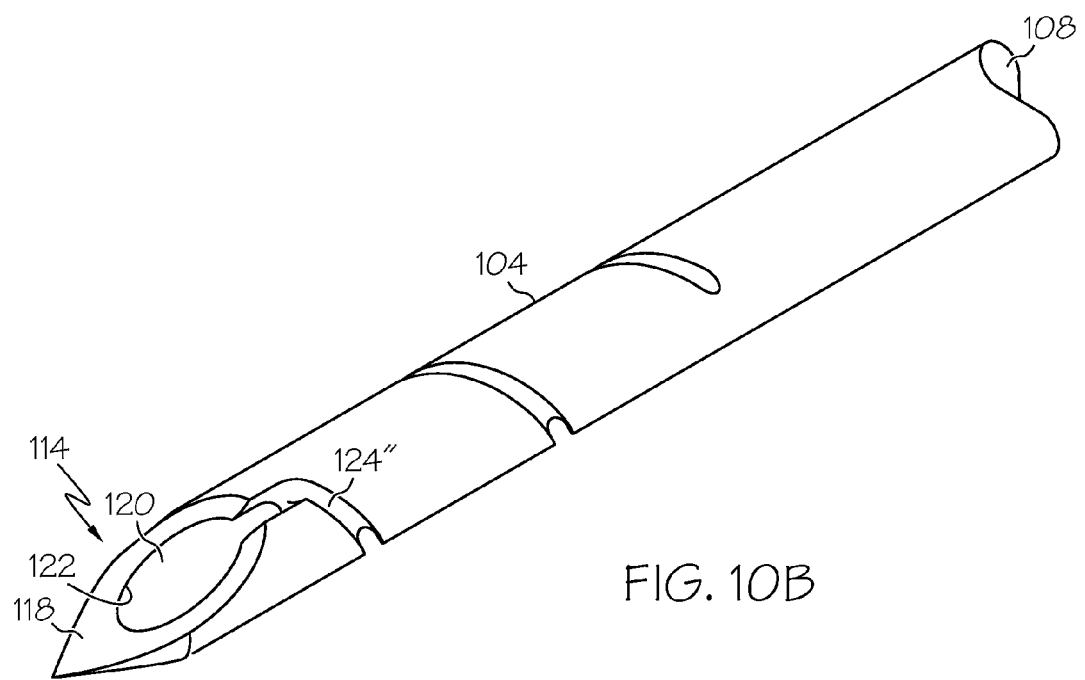
FIG. 10b is an isometric view of the distal end of the filament implant system of FIG. 10a, shown with the filament removed.
Figure 11:
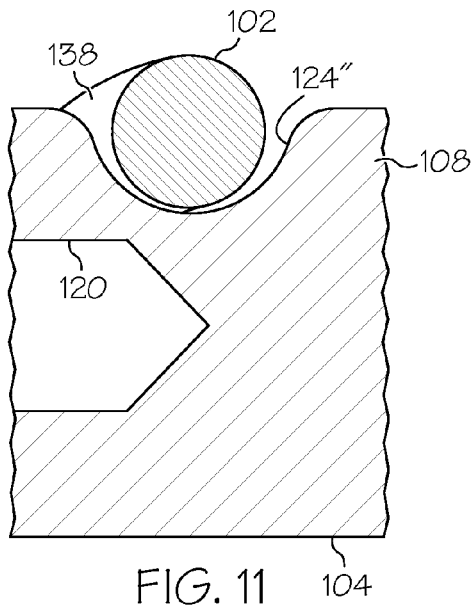

Referring to FIGS. 10a, 10b and 11, in a fourth alternative implementation, the filament 102 may be external of the insertion needle 104 and the distal end 138 of the filament 102 may be received in the recess 120 in the penetrating tip 114, in a manner similar to the implementation shown in FIGS. 5 and 6. However, in the implementation of FIGS. 10a, 10b and 11, the relief 124" may be sized and shaped to closely receive a portion of the distal end 138 of the filament 102, and may extend in a generally spiral or helical path along all or a partially of the length of the elongated body 108 of the insertion needle 104.

Figure 12A:
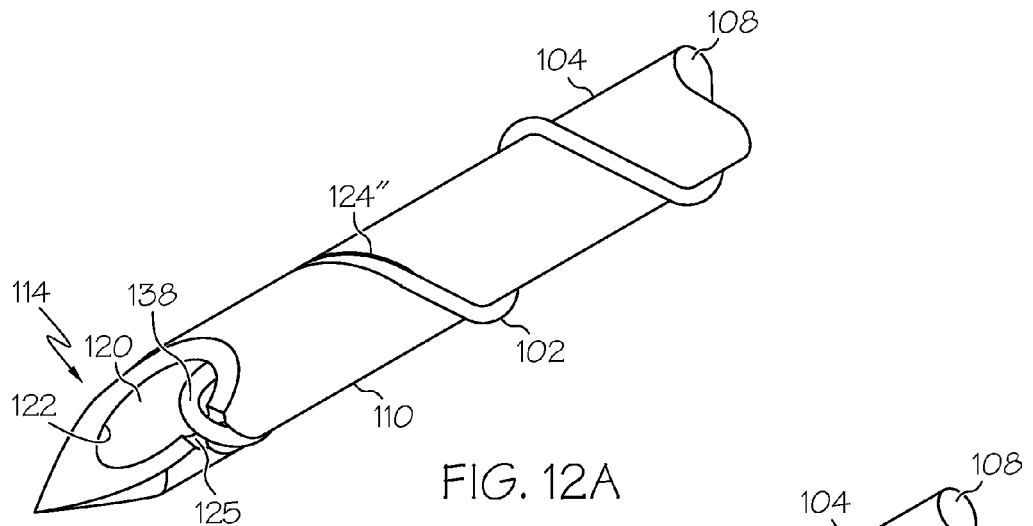
FIG. 12a is an isometric view of a distal end of a filament implant system in accordance with a fifth alternative implementation of the disclosure.
Figure 12B:
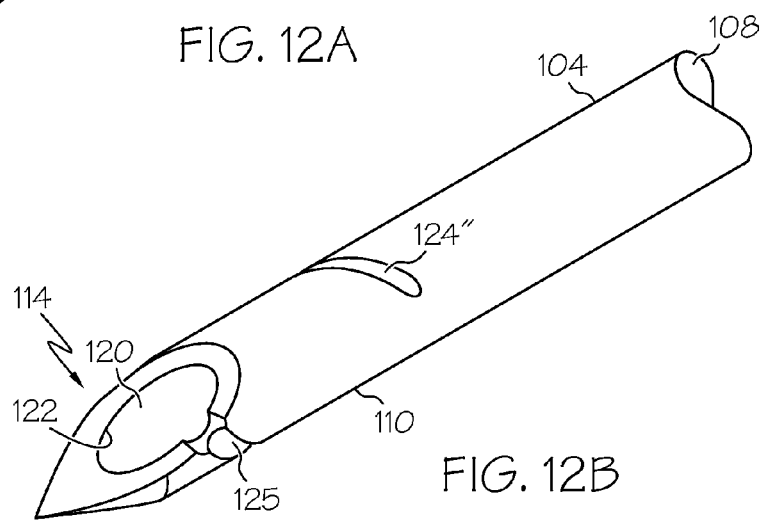
FIG. 12b is an isometric view of the distal end of the filament implant system of FIG. 11a, shown with the filament removed.

Referring to FIGS. 12a and 12b, in a fifth alternative implementation, the filament 102 may extend through a relief 124''' in the insertion needle 104 in a manner similar to the implementation shown in FIGS. 10a, 10b and 11. However, in the implementation of FIGS. 12a and 12b, the relief 124''' may additionally include a notch 125 for receiving the distal end 138 of the filament 102 where the filament 102 enters the recess 120, thereby further minimizing the cross-sectional profile of the distal end 110 of the insertion needle 104.

Figure 13A:
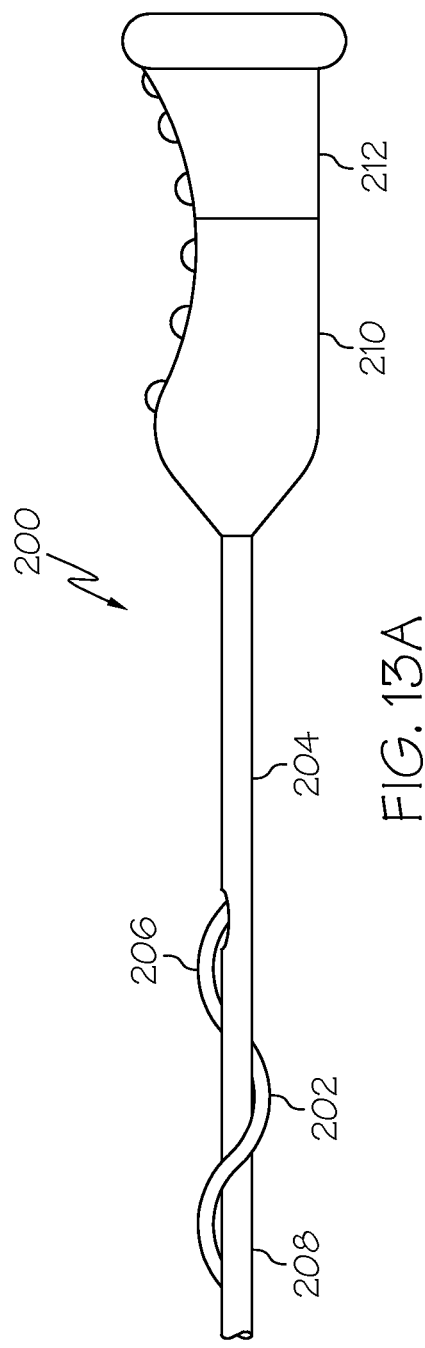
FIG. 13a is a side elevational view of a portion of a filament implant system in accordance with a second aspect of the disclosure, wherein the system is in an engaged configuration.
Figure 13B:
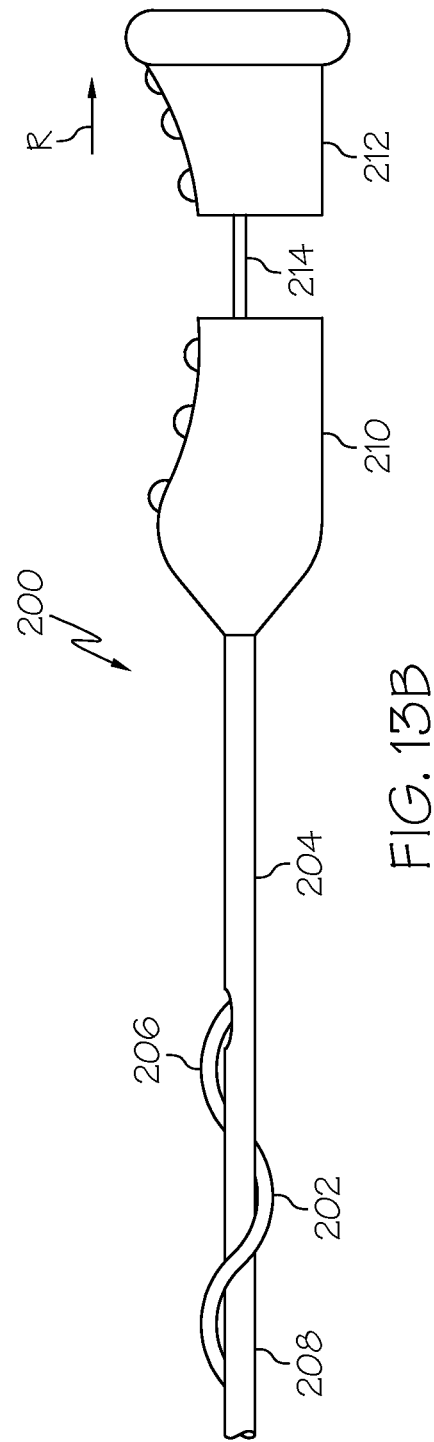
FIG. 13b is a side elevational view of the filament implant system of FIG. 13a, wherein the system is in a disengaged configuration.

As shown in FIGS. 13a and 13b, another aspect of the disclosed filament implant system, generally designated 200, may include a filament 202 and an insertion needle 204. The filament 202 may be generally similar to filament 102, and may include a distal end (not shown) and a proximal end 206. The insertion needle 204 may be generally similar to insertion needle 104, and may include an elongated body 208 and a handle 210. The handle 210 may additionally include a release knob 212 connected to a control rod 214, which may include a beveled distal tip 215 (FIGS. 14a and 14b).

In one implementation, as shown in FIGS. 14a and 14b, the elongated body 208 of the insertion needle 204 may define an internal lumen 216. The lumen 216 may open at a penetrating tip (not shown) disposed at the distal end (not shown) of the elongated body 208, similar to the implementation shown in FIGS. 7a and 7b.

The proximal end 206 of the filament 202 may enter into the lumen 216 by way of an access port 218, and may be releasably engaged by the control rod 214. However, when the release knob 212 is retracted in the proximal direction (arrow R), the control rod 214 may disengage the proximal end 206 of the filament 202, thereby releasing the filament 202 from the insertion needle 204 and allowing the insertion needle 204 to be withdrawn from body tissue (not shown) while leaving the filament 202 behind.

In an alternative implementation, as shown in FIGS. 15a and 15b, the elongated body 208 of the insertion needle 204 may define an internal lumen 216 and the filament 202 may extend through the lumen 216. The lumen 216 may be open at a penetrating tip (not shown) disposed at the distal end (not shown) of the elongated body 208, as described above.

The proximal end 206 of the filament 202 may be releasably engaged by the control rod 214. However, when the release knob 212 (FIG. 13b) is retracted in the proximal direction (arrow R), the control rod 214 may disengage the proximal end 206 of the filament 202, thereby releasing the filament 202 from the insertion needle 204 and allowing the insertion needle 204 to be withdrawn from body tissue (not shown) while leaving the filament 202 behind.

Figure 16A:
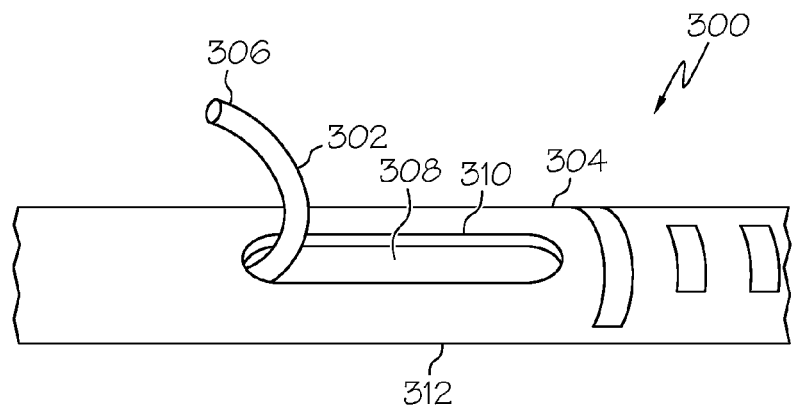
FIG. 16a is an isometric view of a portion of a filament implant system in accordance with a third aspect of the disclosure, wherein the filament is shown engaged with the insertion needle.
Figure 16B:
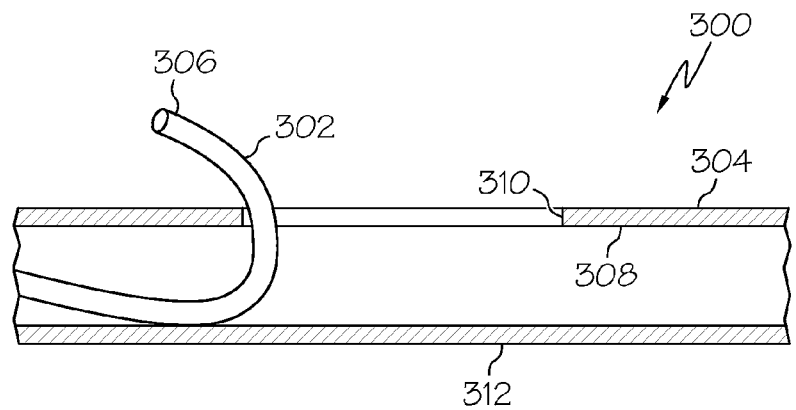
Figure 16C:
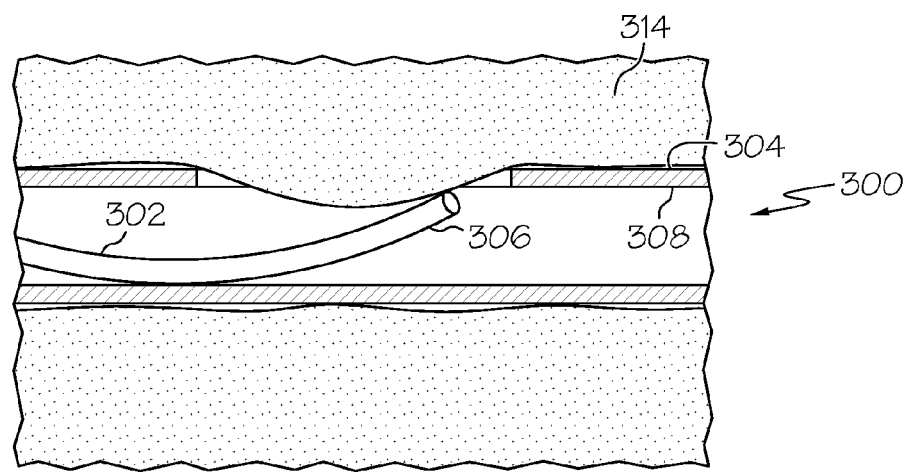
FIG. 16c is a cross-sectional view of the portion of the filament implant system of FIG. 16b positioned in tissue, wherein the filament is shown disengaged from the insertion needle.

As shown in FIGS. 16a, 16b and 16c, another aspect of the disclosed filament implant system, generally designated 300, may include a filament 302 and an insertion needle 304. The filament 302 may be generally similar to filament 102, and may include a distal end (not shown) and a proximal end 306. The insertion needle 304 may be generally similar to insertion needle 104, but the recess 120 (FIG. 5) may be extended to define an elongated lumen 308, and a port 310 in the proximal end 312 of the insertion needle 304 may provide access to the lumen 308.

As shown in FIGS. 16a and 16b, the proximal end 306 of the filament 302 may exit the lumen 308 by way of the port 310, thereby releasably connecting the filament 302 relative to the insertion needle 304. However, as shown in FIG. 16c, when the insertion needle 304 is inserted into tissue 314, the pressure of the tissue 314 may urge the proximal end 306 of the filament 302 into the lumen 308, thereby effectively disengaging the filament 302 from the insertion needle 304.

Figure 17A:
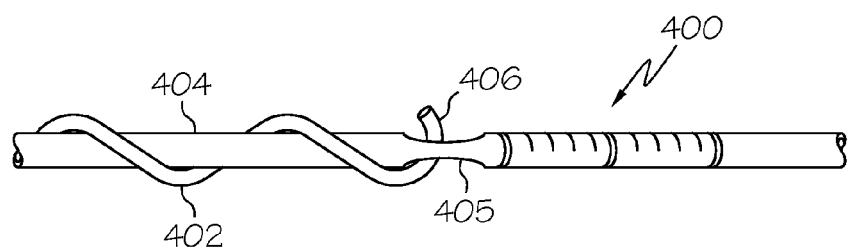
FIG. 17a is an isometric view of a portion of a filament implant system in accordance with a fourth aspect of the disclosure, wherein the filament is shown engaged with the insertion needle.
Figure 17B:
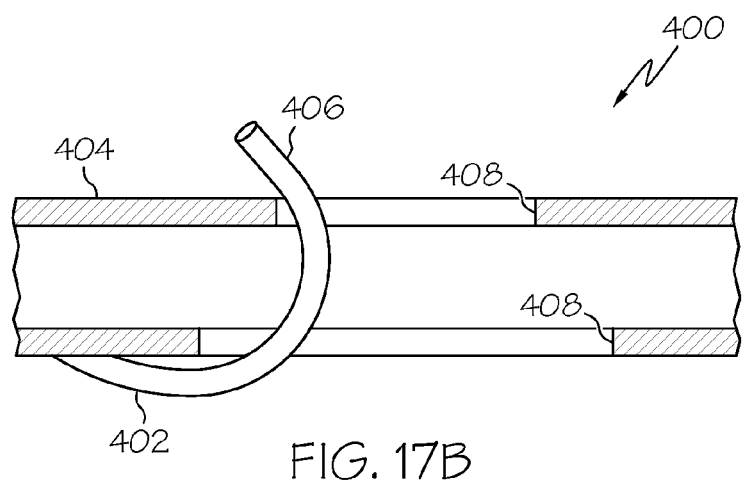
Figure 17C:
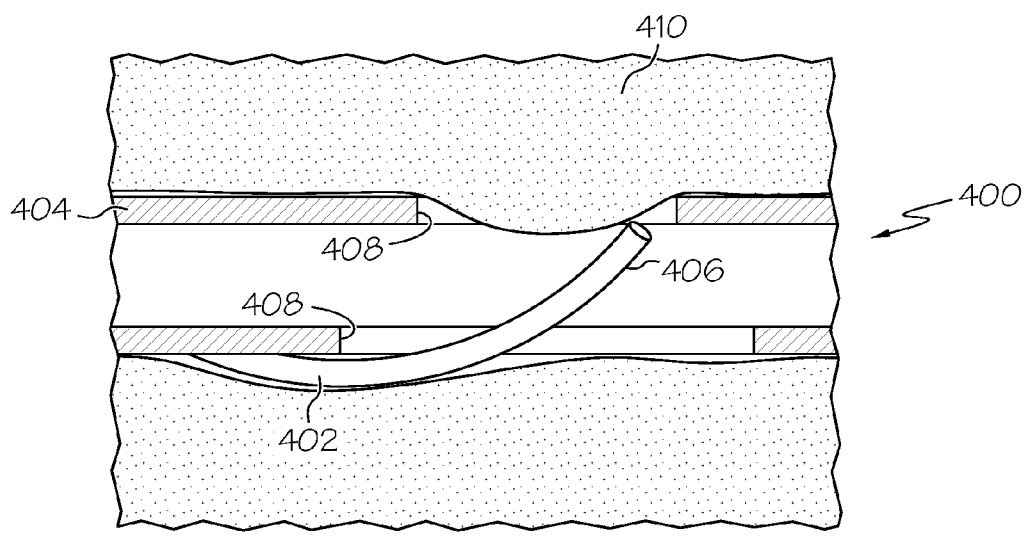
FIG. 17c is a cross-sectional view of the portion of the filament implant system of FIG. 17b positioned in tissue, wherein the filament is shown disengaged from the insertion needle.

As shown in FIGS. 17a, 17b and 17c, yet another aspect of the disclosed filament implant system, generally designated 400, may include a filament 402 and an insertion needle 404. The filament 402 may be generally similar to filament 102, and may include a distal end (not shown) and a proximal end 406. The insertion needle 404 may be generally similar to insertion needle 104, but may include a opening 408 (e.g., a radial opening) therethrough.

As shown in FIGS. 17 and 17b, the filament may be wrapped around the exterior of the insertion needle 404 and the proximal end 406 of the filament 402 may pass through the opening 408, thereby releasably connecting the filament 402 relative to the insertion needle 404. However, as shown in FIG. 17c, when the insertion needle 404 is inserted into tissue 410, the pressure of the tissue 410 may urge the proximal end 406 of the filament 402 out of the opening 408, thereby effectively disengaging the filament 402 from the insertion needle 404.

In yet another aspect, the disclosed filament implant systems may be assembled into a kit. As a first example, a kit may include one or more preloaded filament implant systems. As a second example, a kit may include two or more preloaded filament implant systems of different sizes. As a third example, a kit may include one or more preloaded filament implant systems and instructions for use. As a fourth example, a kit may include a filament implant system and one or more other items, such as drapes, sharps disposable container, topical anesthesia or surgical gloves. As a fifth example, as kit may include a filament implant system and one or more additional filaments for reloading the insertion needle after use.

Accordingly, the disclosed filament implant system and method eliminates the need to exit the tissue during the implantation of filaments into body tissue by enabling users to remotely or automatically release the filament from the insertion needle. Furthermore, the disclosed filament implant system and method may reduce resistance and trauma during insertion, and may guide the user during insertion.

Although various aspects of the disclosed filament implant system and method have been shown and described, modifications may occur to those skilled in the art upon reading the specification. The present application includes such modifications and is limited only by the scope of the claims.

What is claimed is:

1. A filament implant system comprising:
   an insertion needle comprising an elongated body defining a longitudinal axis and having a distal end and a proximal end, said distal end of said elongated body comprising a penetrating tip and a recess, wherein said recess comprises an opening proximate said penetrating tip and longitudinally extends into said elongated body; and
   a filament comprising a hooked portion and a trailing portion, said hooked portion being hooked onto said distal end of said elongated body such that said trailing portion longitudinally extends into said recess,
   wherein said hooked portion of said filament is engaged with said insertion needle when said insertion needle is advanced into tissue distally along said longitudinal axis, and
   wherein said hooked portion of said filament is automatically disengaged from said insertion needle when said insertion needle is withdrawn from said tissue proximally along said longitudinal axis.

2. The filament implant system of claim 1 wherein said recess is an elongated lumen, and wherein said trailing portion is entirely received in said elongated lumen.

3. The filament implant system of claim 1 wherein said elongated body has a cross-sectional thickness of at most 25 gauge.

4. The filament implant system of claim 1 further comprising a handle disposed at said proximal end of said elongated body.

5. The filament implant system of claim 4 wherein said handle includes an alignment feature.

6. The filament implant system of claim 1 wherein said insertion needle further includes a depth scale disposed proximate said proximal end of said elongated body.

7. The filament implant system of claim 1 wherein said filament comprises gold.

8. The filament implant system of claim 1 wherein said filament comprises at least one of a drug, a biologic and a therapeutic agent incorporated therein.

9. A method for implanting a filament in body tissue comprising the steps of:
   providing a filament implant system comprising an insertion needle including an elongated body having a distal end and a proximal end, said distal end of said elongated body including a penetrating tip and a recess, and a filament comprising a hooked portion and a trailing portion, said hooked portion being hooked onto said distal end of said elongated body such that said trailing portion longitudinally extends into said recess;
   advancing said insertion needle into said body tissue, wherein said filament travels with said insertion needle during said advancing step; and
   withdrawing said insertion needle from said body tissue, wherein said hooked portion of said filament is automatically disengaged from said insertion needle during said withdrawing step such that said filament remains in said body tissue.

* * * * *